US00PP30542P3

(12) United States Plant Patent
Pierron-Darbonne

(10) Patent No.: US PP30,542 P3
(45) Date of Patent: May 28, 2019

(54) STRAWBERRY PLANT NAMED 'PLANASA 0955'

(50) Latin Name: ***Fragaria* x *ananassa* Duchesne ex Rozier**
Varietal Denomination: Planasa 0955

(71) Applicant: Plantas de Navarra, S.A., Navarra (ES)

(72) Inventor: Alexandre Pierron-Darbonne, Pamplona (ES)

(73) Assignee: PLANTAS DE NAVARRA, S.A., Valtierra, Navarra (ES)

( * ) Notice: Subject to any disclaimer, the term of this patent is extended or adjusted under 35 U.S.C. 154(b) by 0 days.

(21) Appl. No.: 15/731,689

(22) Filed: Jul. 17, 2017

(65) Prior Publication Data

US 2018/0027712 P1 Jan. 25, 2018

(30) Foreign Application Priority Data

Jul. 22, 2016 (QZ) ..... PBR 2016/1836

(51) Int. Cl.
*A01H 5/08* (2018.01)
*A01H 6/74* (2018.01)

(52) U.S. Cl.
USPC ..... Plt./208
CPC ..... *A01H 6/7409* (2018.05); *A01H 5/08* (2013.01)

(58) Field of Classification Search
USPC ..... Plt./208, 209
CPC ..... A01H 5/0893
See application file for complete search history.

*Primary Examiner* — Kent L Bell
(74) *Attorney, Agent, or Firm* — Knobbe, Martens, Olson & Bear, LLP

(57) ABSTRACT

Descried herein is a new and distinct strawberry variety with varietal denomination 'Planasa 0955', characterized by a combination of traits which include, but are not limited to, inflorescence that appears level with the foliage, larger size of calyx relative to corolla and abundant production of medium to large-sized medium red colored, conical shaped, and firm fruits, with orange red colored flesh, with medium time of flowering and ripening. 'Planasa 0955' is a not remontant variety.

15 Drawing Sheets

Botanical classification: *Fragaria* x *ananassa* Duchesne ex Rozier.

Variety denomination: The new plant has the varietal denomination 'Planasa 0955'.

CROSS-REFERENCE TO RELATED APPLICATIONS

This application claims the benefit of European Community Plant Variety Office Application No. 2016/1836, for a strawberry variety named 'Planasa 0955,' filed on Jul. 22, 2016, the entirety of which is incorporated by reference herein.

BACKGROUND

Disclosed herein is a new and distinct strawberry variety. The varietal denomination of the new variety is 'Planasa 0955'. The new variety was designated by the breeder as '09.24.197'. The new variety of strawberry was created in a breeding program by crossing two parents in 2009 in Cartaya (Huelva), Spain about 7° W, 37° N, 45 feet elevation (15 meters high); in particular, by crossing as seed parent an undistributed strawberry parent designated '09-024' (unpatented) and as pollen parent an undistributed strawberry parent designated '03-98' (unpatented). Each parent is a selection from breeder's program and has not been commercialized.

The resulting seedling of the new variety was grown and asexually propagated by Alexandre Pierron-Darbonne by runners in Segovia, Spain, 3° 59'W., 41° 22'N., 2742 feet elevation and it was successively propagated by runners first into a Screen-House, and after in the fields. Plants of the new variety were further asexually propagated and extensively tested. In order to establish and bring to health the initial head plants, mother plants that had developed several stolons were subjected to a heat treatment, or Thermotherapy, at 36° C.-37° C. for 3 to 4 weeks. After that treatment, apical meristems were cut and developed (1 apical meristem corresponding to 1 rooting plant) in an in vitro culture for 5 to 6 weeks. This propagation and testing has demonstrated that the combination of traits disclosed herein which characterize the new variety are fixed and retained true to type through successive generations of asexual reproduction.

The growing period in Cartaya (Huelva), Spain, about 7° W, 37° N, 45 feet elevation (15 meters high), where the observations were made, is between about October 13 and May 11 of each year with a date of first flowering on November 11. The location where the observations were made is Cartaya (Huelva), Spain and it is believed to apply to plants grown under similar conditions of soil and climate elsewhere. 'Planasa 0955' is a short day variety that benefits from induction to flowering by chilling, usually a few hours are sufficient, preferably at temperatures of 7° C. or less. Normally, the minimum number of hours is accumulated in the field during several days.

SUMMARY

Among the characteristics which distinguish the new variety from other varieties are a combination of traits which include inflorescences that appear level with the foliage, larger size of calyx relative to corolla and abundant production of medium red colored, conical shaped, and firm fruit, medium to large fruit size, orange red colored flesh, and medium time of flowering and ripening. 'Planasa 0955' is a not remontant variety.

The new variety 'Planasa 0955' is distinguished from other cultivars by showing the inflorescence at same level with the foliage, the shape of the base of terminal leaflet is acute, it shows a conical shape fruit with a medium red color, the fruit is firm and it shows a medium to large size with an orange red colored flesh and it has medium flowering and ripening times.

COMPARISON TO THE PARENTS

The new variety 'Planasa 0955' is distinguished therefrom its Seed parent '09-024' (unpatented) in that the seed parent length in relation to width of terminal leaflet is equal, the shape of base in terminal leaflet is obtuse, the seed parent shows a medium fruit size.

The new variety 'Planasa 0955' is distinguished there from its pollen parent '03-98' (unpatented) in that in the pollen parent, the leaf color of upper side is dark green with medium glossiness, the flower of pollen parent shows a same size of calyx in relation to corolla.

COMPARISON TO CLOSEST VARIETY

The new variety 'Planasa 0955' is closest to the variety 'Sabrina' (U.S. Plant Pat. No. 22,506) but is distinguished by the following characteristics possessed by 'Planasa 0955' which are different, or not possessed by, 'Sabrina' (U.S. Plant Pat. No. 22,506).

Leaf of 'Sabrina' (U.S. Plant Pat. No. 22,506) shows an R.H.S. green group color in the upperside (near 135 A to 136 A), whereas the new variety 'Planasa 0955' shows an R.H.S. green group color in the upperside (near 141 B to 143 A).

'Sabrina' (U.S. Plant Pat. No. 22,506) shows a red fruit color (R.H.S. red group near 43 B to 43 A), whereas in 'Planasa 0955' it is a medium red fruit color (R.H.S. red group near 44 B to 44 A).

Color of flesh in fruits of 'Sabrina' (U.S. Plant Pat. No. 22,506) is red (R.H.S. red group near 41 B to 41 A), whereas the color of flesh in fruits of 'Planasa 0955' is orange red (R.H.S. orange-red group near 33 B to 33 A), lightening toward the center.

Plant growth habit is upright in 'Planasa 0955' whereas it is semi-upright in 'Sabrina' (U.S. Plant Pat. No. 22,506).

Stolon anthocyanin coloration is absent or very weak in 'Planasa 0955' and medium in 'Sabrina' (U.S. Plant Pat. No. 22,506).

The shape of base of terminal leaflet is acute in 'Planasa 0955'. In comparison, it is obtuse in 'Sabrina' (U.S. Plant Pat. No. 22,506).

Petiole length is medium to long in 'Planasa 0955' and long in 'Sabrina' (U.S. Plant Pat. No. 22,506).

The arrangement of flower petals is touching in 'Planasa 0955,' whereas it is overlapping in 'Sabrina' (U.S. Plant Pat. No. 22,506).

Petal length/width ratio is equal in 'Planasa 0955'. In comparison, it is moderately longer in 'Sabrina' (U.S. Plant Pat. No. 22,506).

The length/width ratio of fruit in 'Planasa 0955' is moderately longer whereas length/width ratio in 'Sabrina' (U.S. Plant Pat. No. 22,506) is much longer than broad.

The fruit size in 'Planasa 0955' is medium whereas in 'Sabrina' (U.S. Plant Pat. No. 22,506) it is large.

The difference of shape of primary and secondary fruits is none to very slight in 'Planasa 0955'. In comparison, it is moderate in 'Sabrina' (U.S. Plant Pat. No. 22,506).

The fruit color in 'Planasa 0955' is medium red fruit color whereas 'Sabrina' (U.S. Plant Pat. No. 22,506) shows a dark red fruit color.

In the fruit, the width of the band without achenes is absent or very narrow in 'Planasa 0955' whereas it is narrow in 'Sabrina' (U.S. Plant Pat. No. 22,506).

Insertion/position of achenes in fruits of 'Planasa 0955' is below surface, whereas in 'Sabrina' (U.S. Plant Pat. No. 22,506) it is level with surface.

Attitude of sepals in the fruit is upwards and outwards in 'Planasa 0955' whereas it upwards in 'Sabrina' (U.S. Plant Pat. No. 22,506).

Diameter of calyx in relation to diameter of fruit is slightly smaller in 'Planasa 0955' whereas it is the same size in 'Sabrina' (U.S. Plant Pat. No. 22,506).

Differences in shape of base in the terminal leaflet of 'Planasa 0955' (designated 09.24.197) and 'Sabrina' (U.S. Plant Pat. No. 22,506) are shown in FIG. 5 and FIG. 6.

Differences in the upperside color of leaf of 'Planasa 0955' (designated 09.24.197) and 'Sabrina' (U.S. Plant Pat. No. 22,506) are shown in FIG. 5.

Differences in the arrangement of petals in the flower of 'Planasa 0955' (designated 09.24.197) and 'Sabrina' (U.S. Plant Pat. No. 22,506) are shown in FIG. 11.

Differences in fruit size, fruit color and fruit length, in relation to width, of 'Planasa 0955' (designated 09.24.197) and 'Sabrina' (U.S. Plant Pat. No. 22,506) are shown in FIG. 15.

These differences are maintained during the harvest season.

BRIEF DESCRIPTION OF THE ILUSTRATIONS

The accompanying photographs show typical specimens of the new variety, designated 09.24.197 in the illustrations, including fruit, foliage and flower, in color as nearly true as it is reasonably possible to make in color illustrations of this character.

The plants depicted in the drawings were planted October 13 in Cartaya (Huelva), Spain, about 7° W, 37° N, 45 feet elevation (15 meters high).

Drawings/photographs were taken March-April (about March 23 and April 11): minimum temperate about 10 to 12° Centigrade, maximum temperate about 22 to 24° Centigrade.

Figure 1:
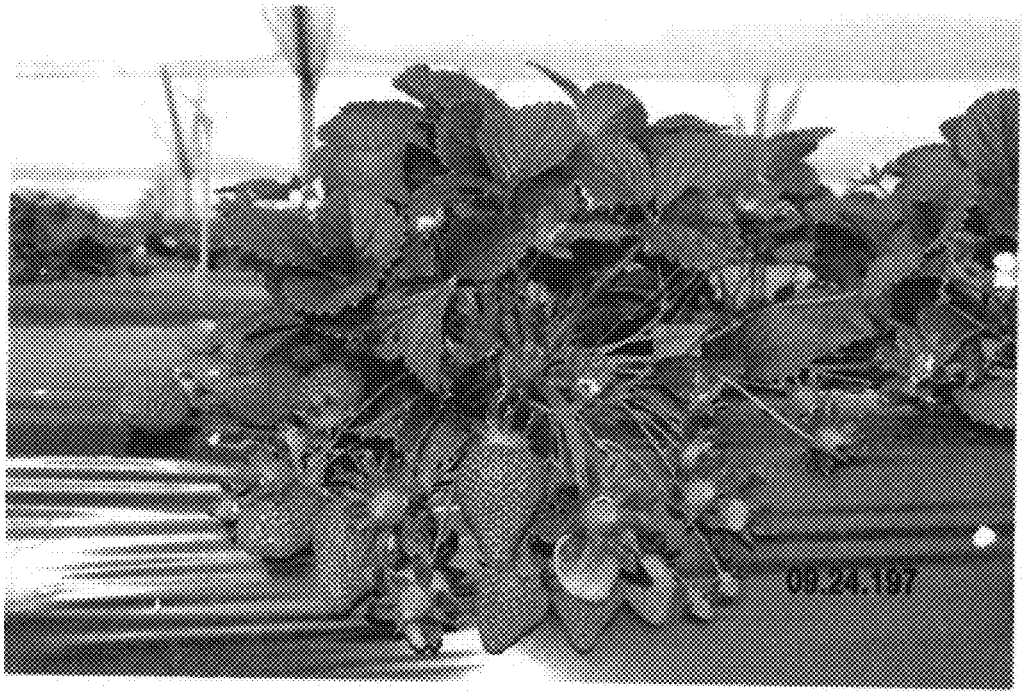
FIG. 1 shows several plants of the new variety (designated 09.24.197) with several medium red colored and conical shape fruits.
Figure 2:
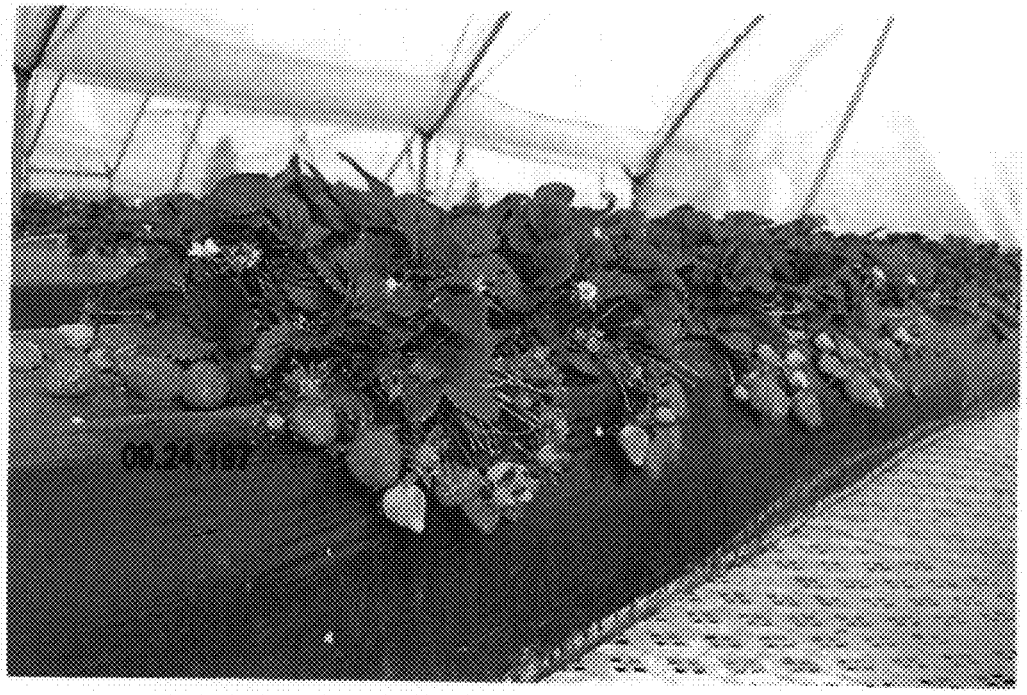
FIG. 2 shows several plants of the new variety (designated 09.24.197) which exhibit an upright habit, a high density plant and the position of the inflorescence relative to foliage is at same level.
Figure 3:
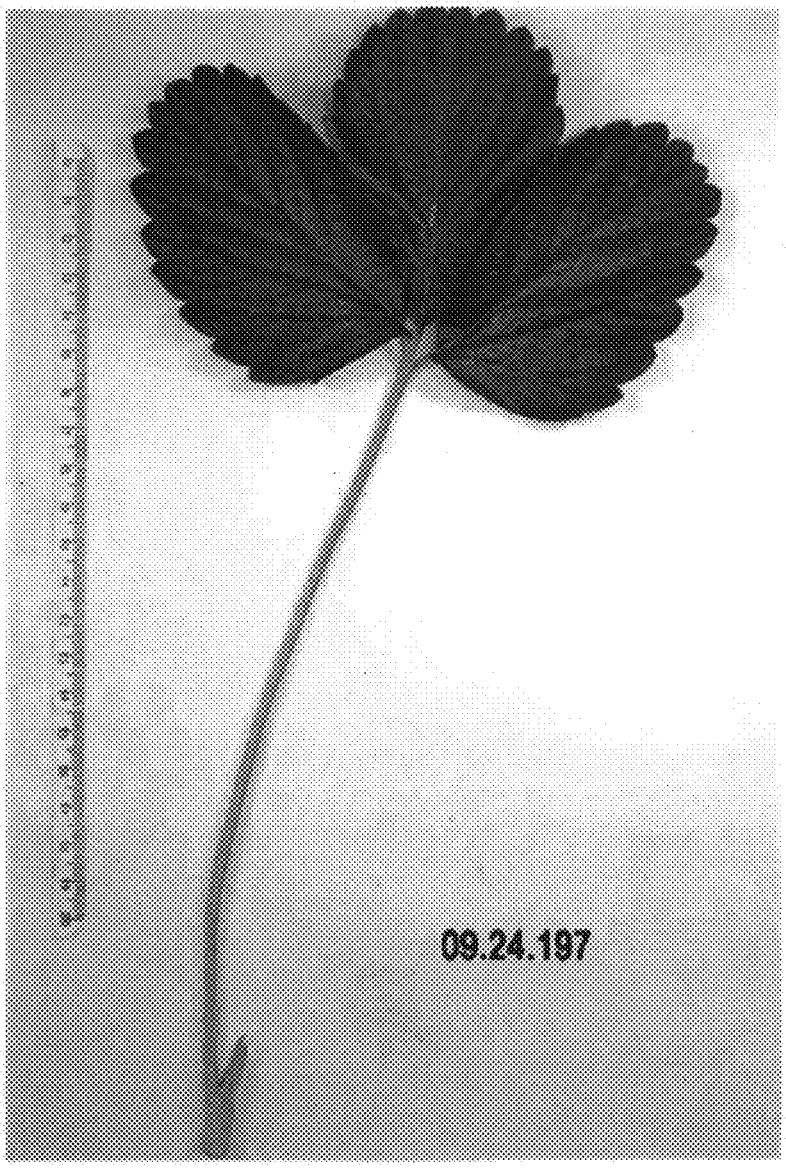
FIG. 3 shows the upperside of a complete leaf of the new variety (designated 09.24.197). In it we can see that the leaf color of upperside is R.H.S. green group color (near 141 B to 143 A).
Figure 4:
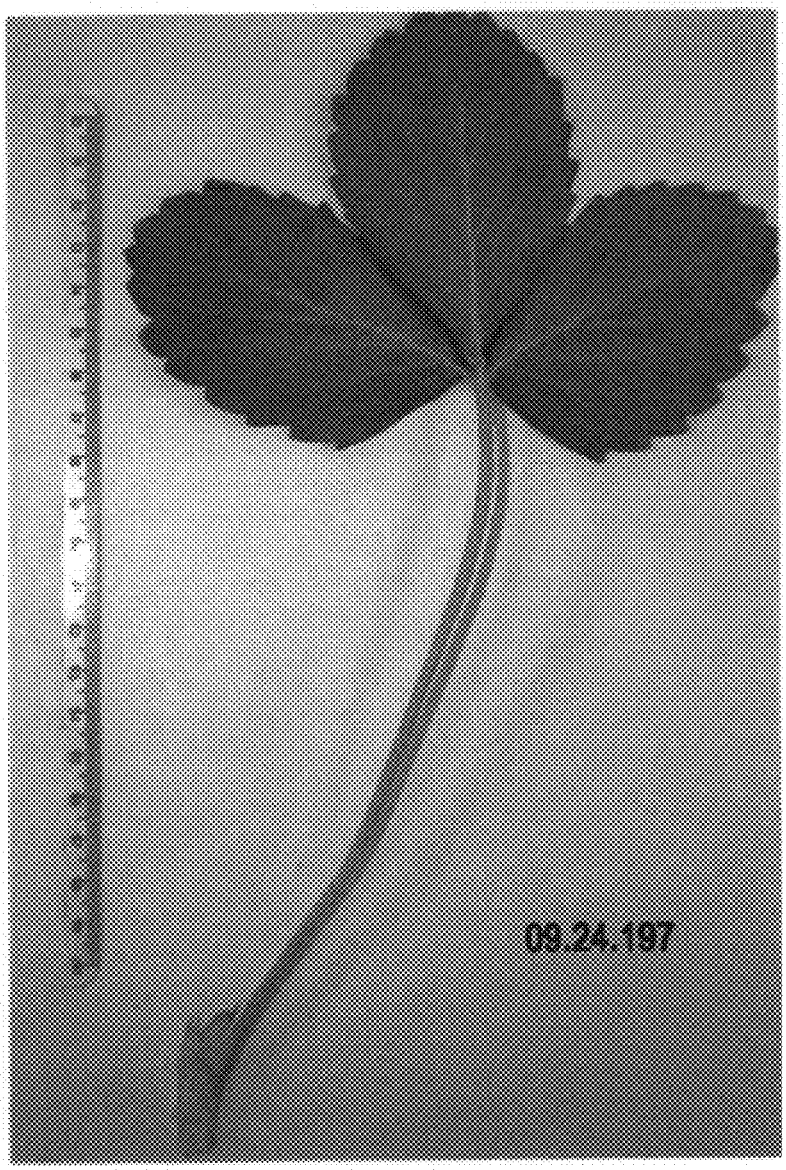
FIG. 4 shows the underside of a complete leaf of the new variety (designated 09.24.197). The leaf color of underside is R.H.S. yellow-green group color (near 146 B to 146 A).
Figure 5:
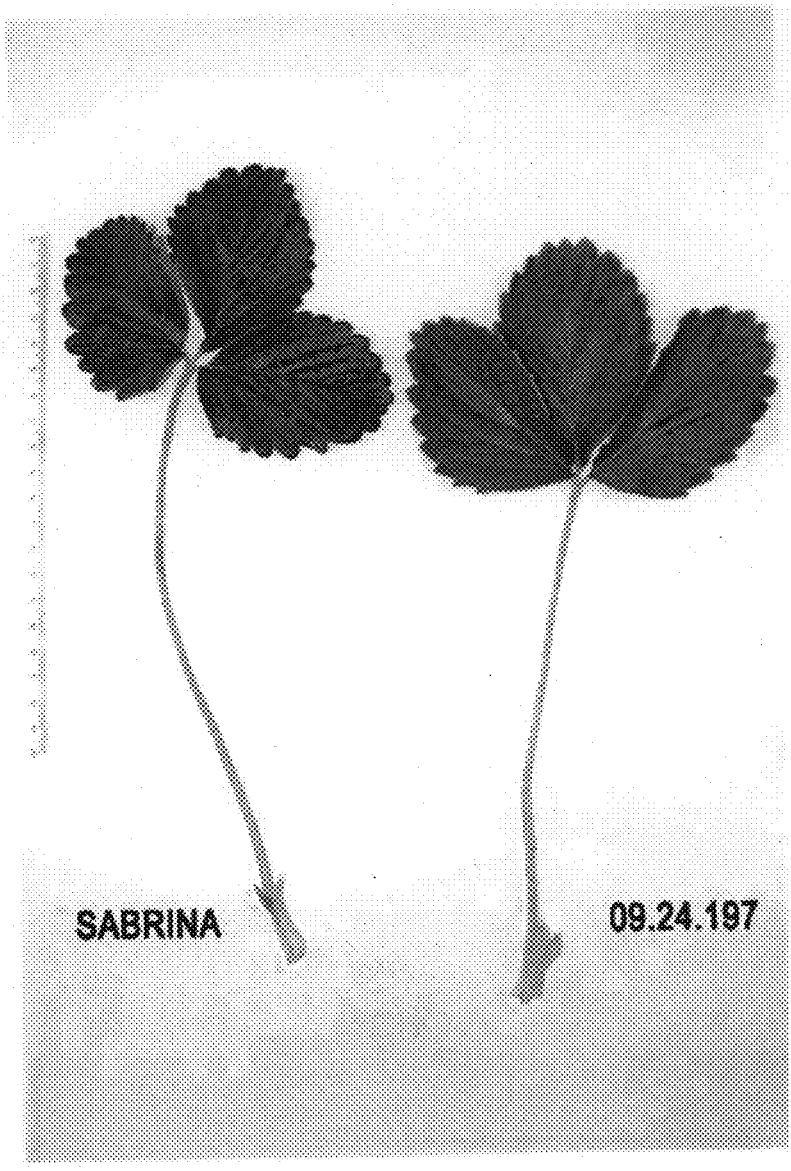

FIG. 5 shows the upperside of a complete leaf of the new variety (designated 09.24.197), with a R.H.S. green group color (near 141 B to 143 A), in comparison with the upperside of a complete leaf of strawberry variety 'Sabrina' (U.S. Plant Pat. No. 22,506), with a R.H.S. green group color (near 135 A to 136 A).

Figure 6:
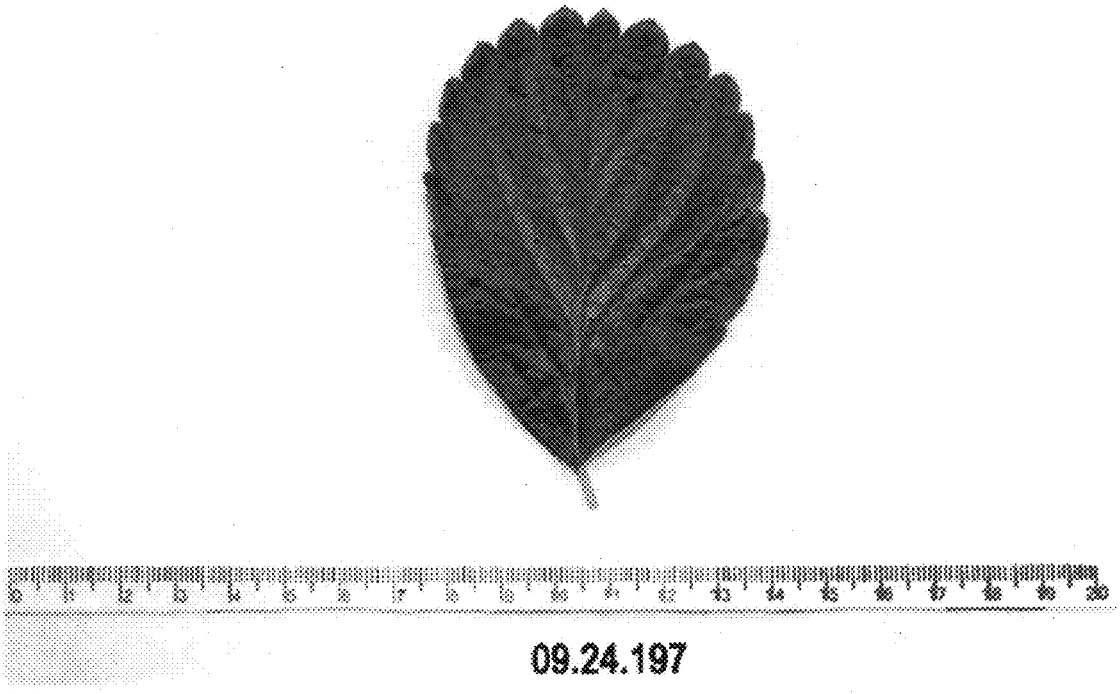
Figure 7:
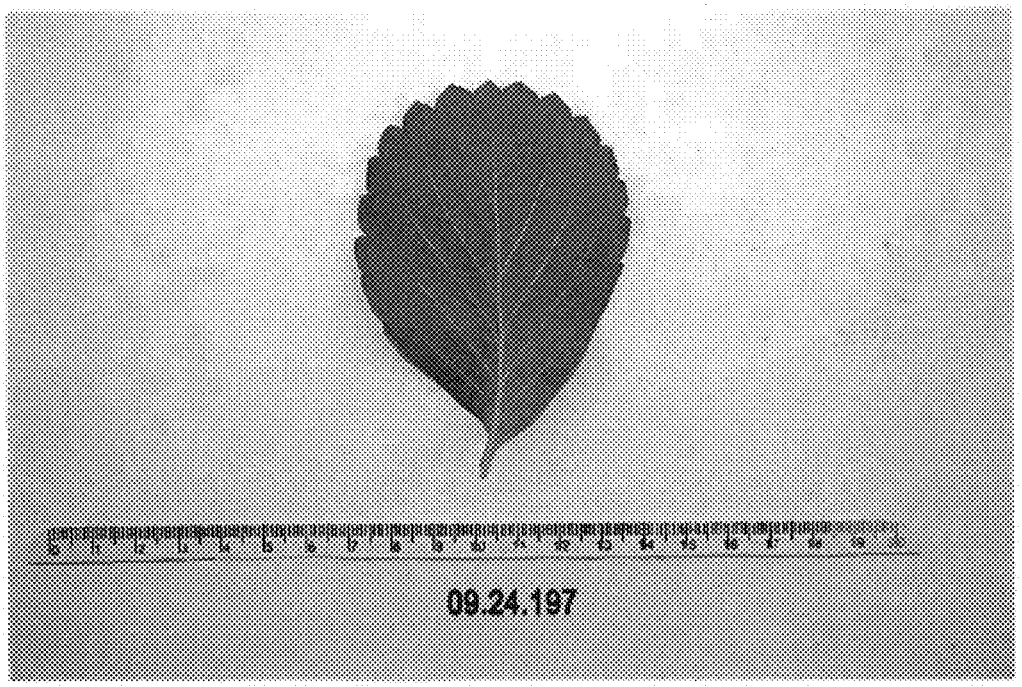

FIG. 6 and FIG. 7 show the upperside and the underside, respectively, of the terminal leaflet of the new variety (designated 09.24.197). We can appreciate the acute shape of the base.

Figure 8:
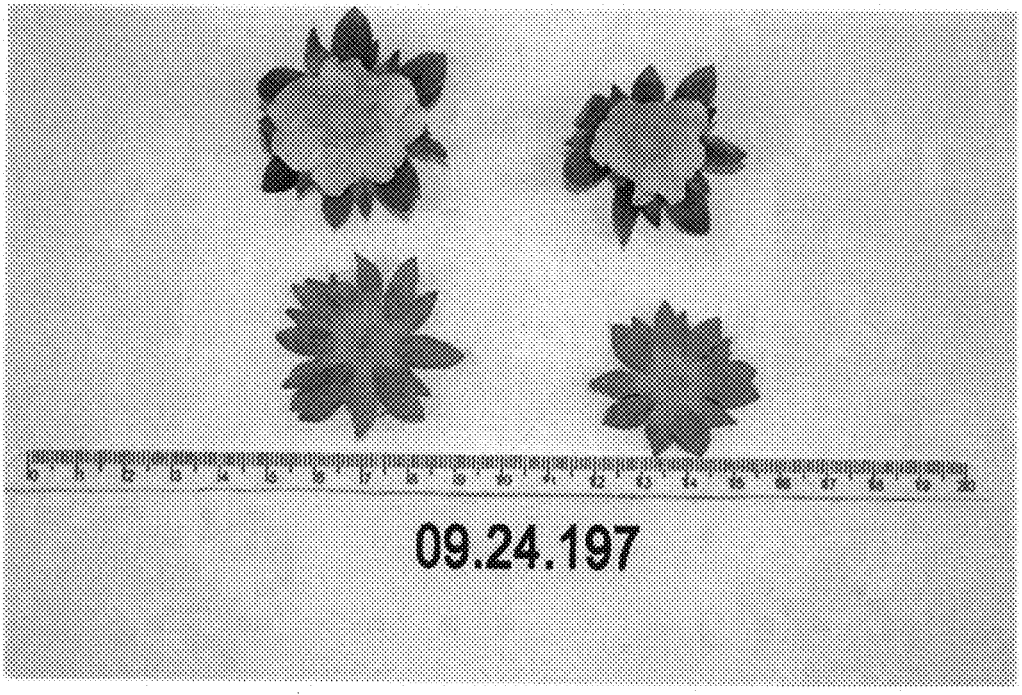

FIG. 8 shows several flowers of the new variety (designated 09.24.197).

Figure 9:
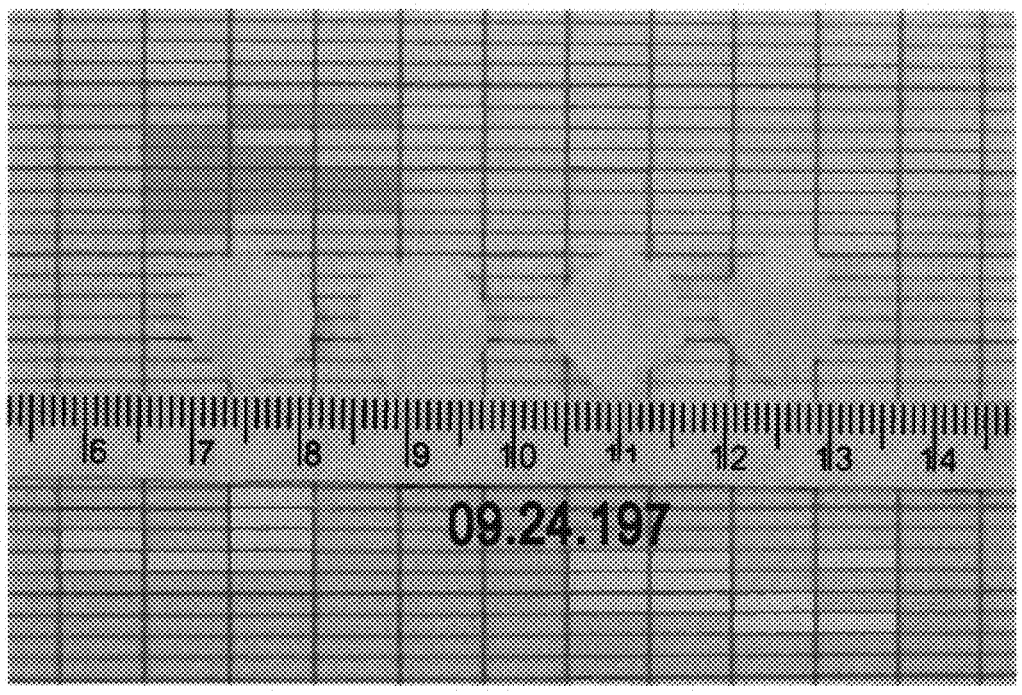

FIG. 9 shows several petals of the new variety (designated 09.24.197).

Figure 10:
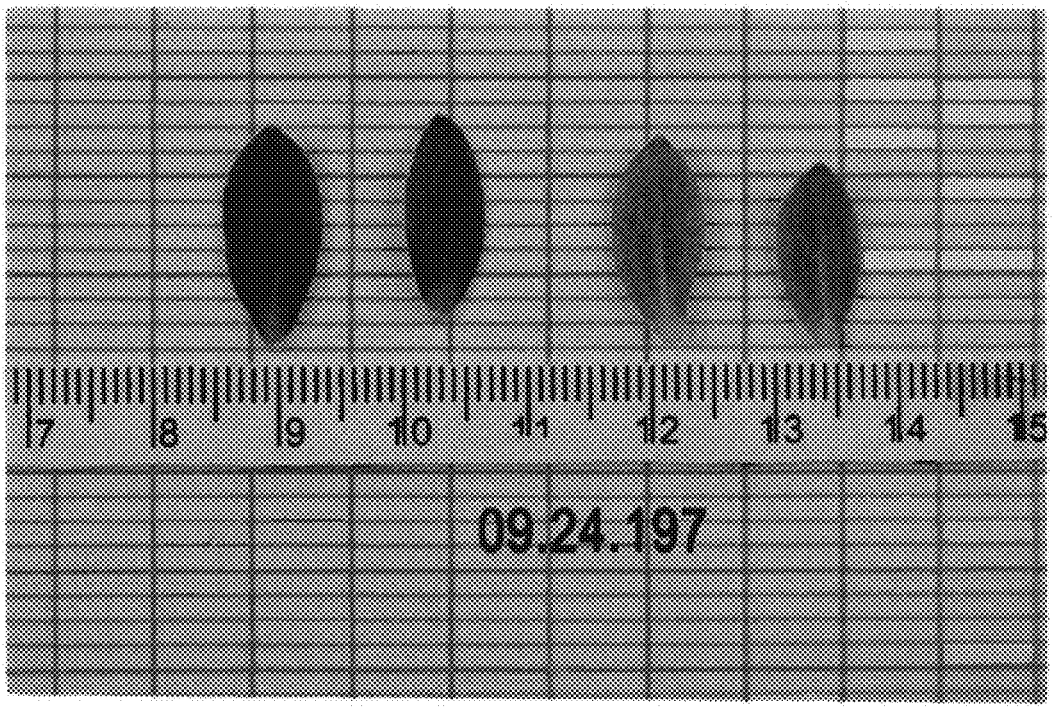

FIG. 10 shows upperside and underside of typical sepals of the new variety (designated 09.24.197).

Figure 11:
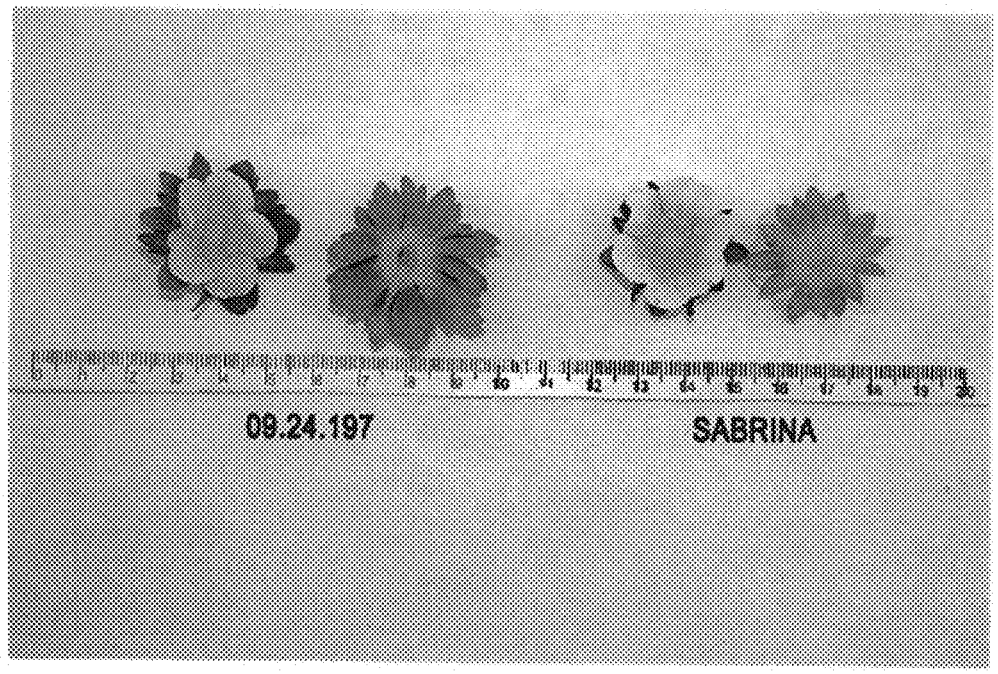

FIG. 11 shows the comparison between flowers of the new variety (designated 09.24.197) and the strawberry variety 'Sabrina' (U.S. Plant Pat. No. 22,506).

Figure 12:
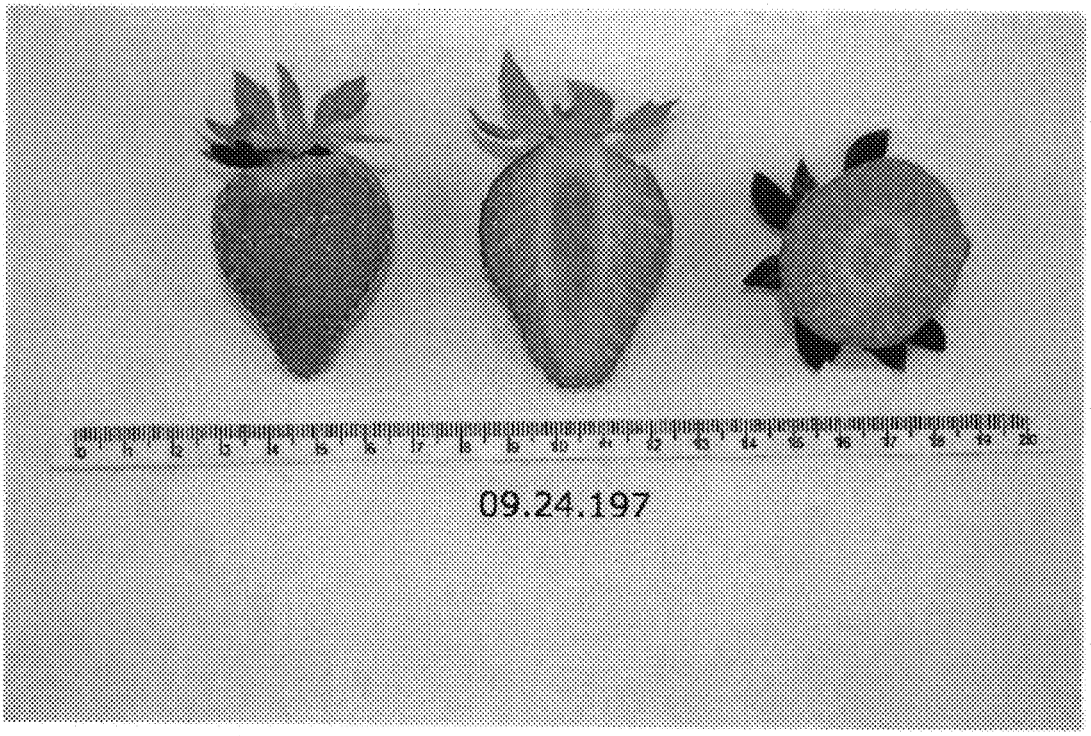

FIG. 12 shows typical fruit of the new variety (designated 09.24.197) whole, sliced and in cross section, illustrating the typical medium red fruit color (R.H.S. red group near 44 B to 44 A), the typical orange red flesh coloration (R.H.S. orange-red group near 33 B to 33 A) lightening toward the center, with an absent or weakly expressed hollow center.

Figure 13:
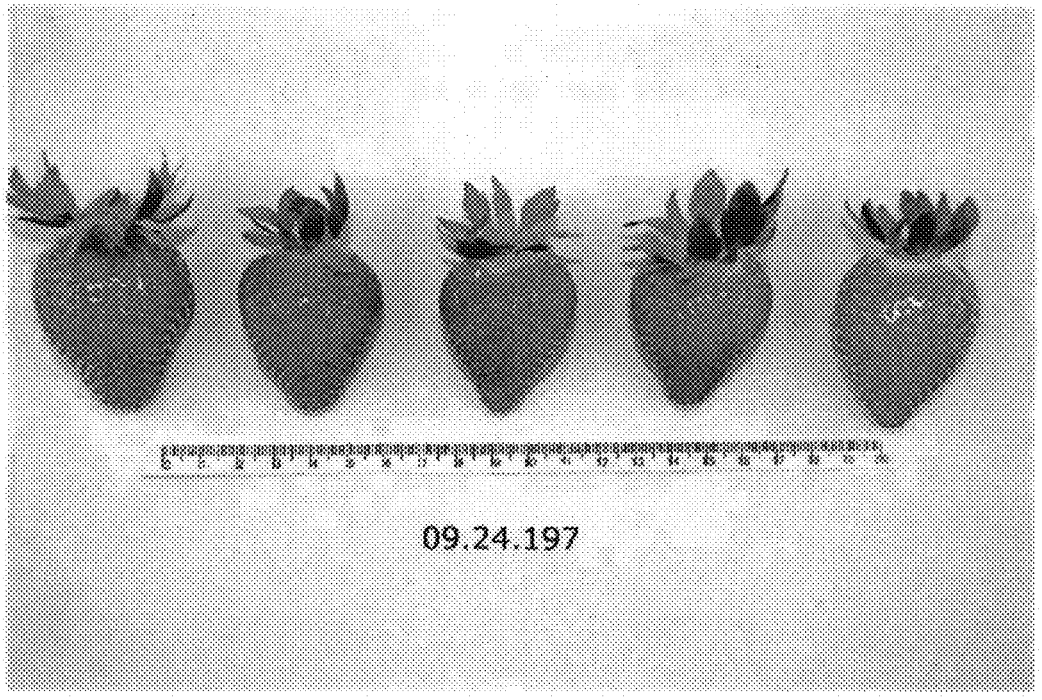

FIG. 13 shows several typical fruits of the new variety (designated 09.24.197) illustrating the typical conical shape and red fruit color (R.H.S. red group near 44 B to 44 A).

Figure 14:
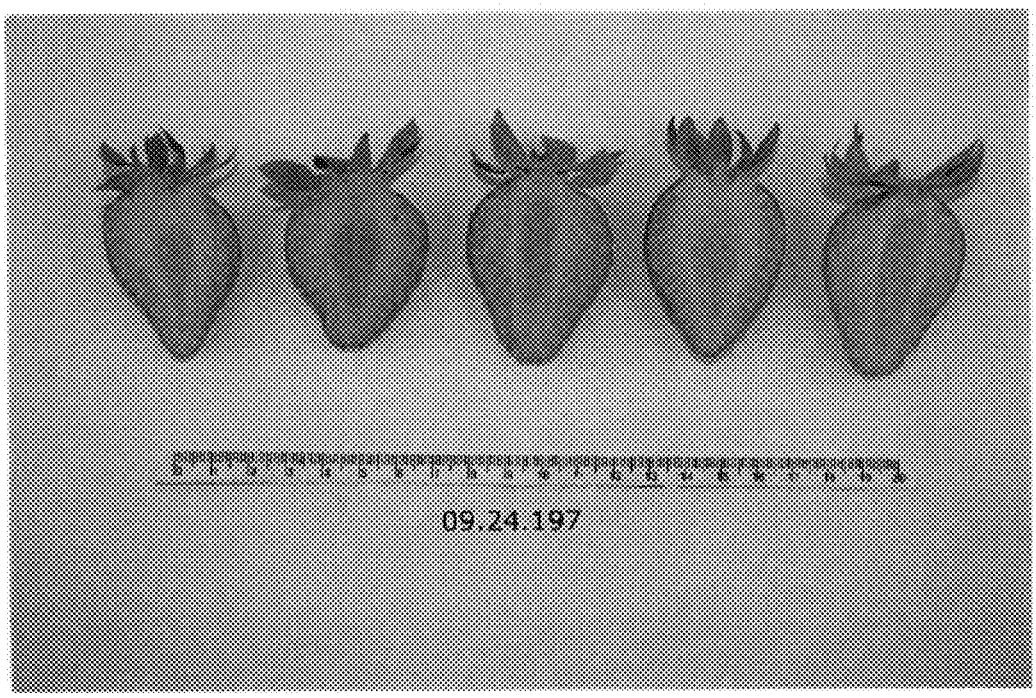

FIG. 14 shows several typical fruits of the new variety (designated 09.24.197) in cross section illustrating the typical orange red flesh coloration (R.H.S. orange-red group near 33 B to 33 A) lightening toward the center, with an absent or weakly expressed hollow center.

Figure 15:
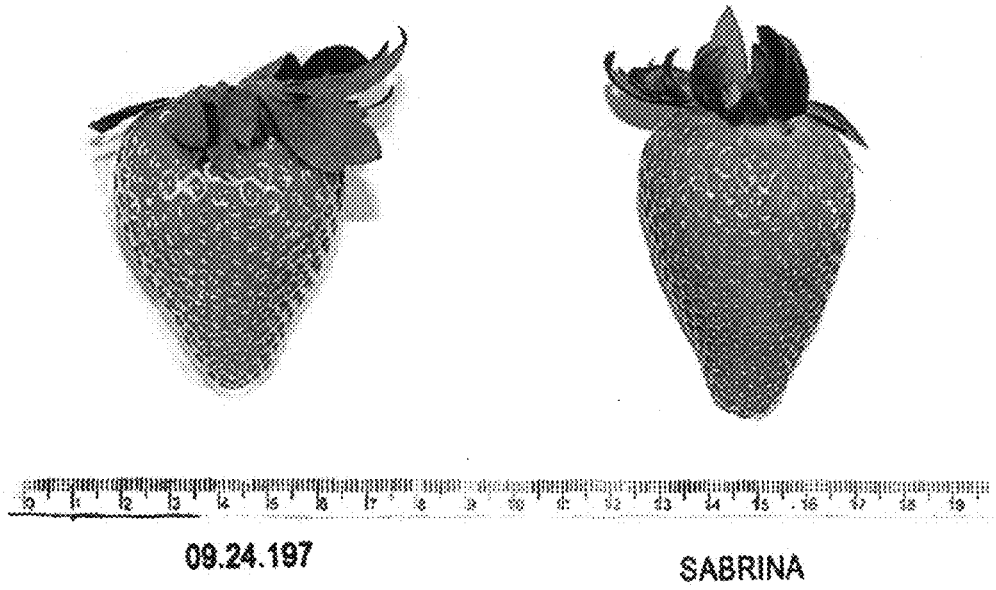

FIG. 15 shows the comparison between whole fruits of the new variety (designated 09.24.197) and the strawberry variety 'Sabrina' (U.S. Plant Pat. No. 22,506). In it we can see that the fruit size in 'Sabrina' (U.S. Plant Pat. No. 22,506) is larger than in the new variety (designated 09.24.197) and the fruits of the strawberry variety 'Sabrina' (U.S. Plant Pat. No. 22,506) show a red fruit color (R.H.S. red group near 43 B to 43 A), whereas in the new variety (designated 09.24.197) the fruits show a red fruit color (R.H.S. red group near 44 B to 44 A).

DESCRIPTION OF THE NEW VARIETY

The following description is in accordance with UPOV terminology and the color terminology herein is in accordance with The Royal Horticultural Society Colour Chart (R.H.S.C.C.), 3rd edition published in 1995.

The color descriptions and other phenotypical descriptions may deviate from the stated values and descriptions depending upon variation in environmental, seasonal, climatic and cultural conditions.

Throughout this specification, color names beginning with a small letter signify that the name of that color, as used in common speech is aptly descriptive. Color names beginning with capital letter designate values based upon The R.H.S. Colour Chart published by The Royal Horticultural Society, London, England, 1995.

The following detailed description of the new variety is based upon observations taken of plants and fruits grown under tunnel, in Cartaya (Huelva), Spain, 7° W., 37° N., 45 feet elevation (15 meters high).

PROPAGATION

The new variety is principally propagated by way of runners. Although propagation by runners is presently preferred, other known methods of propagating strawberry plants may be used. Strawberries root well after transplanting.

The term "blistering" used herein refers to the texture or rugosity or surface undulation inherent to leaves and is generally a constant characteristic.

'Planasa 0955' is a short day variety that needs an induction to flowering by chilling, such as occurs at a high elevation nursery (fresh plant) or with cold storage (referred to as a frigo plant). Usually a short time is sufficient. 'Planasa 0955' is self-fertile. It produces large quantities of pollen throughout the seasons and pollination is generally good as there are very few malformed fruit.

Trials were pursued in Cartaya (Huelva), Spain, about 7° W, 37° N, 45 feet elevation (15 meters high). Plants were planted on October 13 with a sample size of two repetitions and 250 plants per repetition. After planting, plants are grown in raised beds covered with plastic and with small holes in plastic walls, under tunnels. Water and fertilizer are applied through drip irrigation.

GENERAL

Table 1

Table 1 shows the Accumulated production of Commercial Quality Fruit (g/plant) of the new variety 'Planasa 0955' when compared to its closest varieties 'Sabrina' and 'Florida Radiance' (U.S. Plant Pat. No. 20,363) during the months of February, March, April and May.

| Variety | 26-Fb | 30-Mr | 24-Ap | 11-My |
|---|---|---|---|---|
| 'Planasa 0955' | 175 | 522 | 923 | 1175 |
| 'SABRINA' | 179 | 325 | 746 | 1073 |
| 'Florida Radiance' | 262 | 564 | 1014 | 1252 |

Table 2

Table 2 shows the Total Yield from October 13 and fruit weight average of the new variety 'Planasa 0955' when compared to its closest varieties 'Sabrina' and 'Florida Radiance' to May 11.

| Variety | 1st + 2nd Quality Fruit | TOTAL (1st Quality + 2nd Quality) | Weight (g/fruit) |
|---|---|---|---|
| 'Planasa 0955' | 1175 + 250 | 1425 | −26 − 25 |
| 'SABRINA' | 1073 + 283 | 1356 | 27 − 25 |
| 'Florida Radiance' | 1252 + 170 | 1422 | 26 − 25 |

Table 3

Table 3 shows the Production Total, to May 11 of First Quality Fruit (1st quality) and Second Quality Fruit (2nd quality) in g/plant, of the new variety 'Planasa 0955' when compared to its closest varieties 'Sabrina' and 'Florida Radiance'.

| Variety | 1st Quality | 2nd Quality | TOTAL (1st Quality + 2nd Quality) | % 2nd Quality |
|---|---|---|---|---|
| 'Planasa 0955' | 1175 | 250 | 1425 | 17.5 |
| 'SABRINA' | 1073 | 283 | 1356 | 21 |
| 'Florida Radiance' | 1252 | 170 | 1422 | 12 |

% 2nd Quality = (2nd Quality/TOTAL) × 100

Table 4

Table 4 shows the Weight (g/Fruit) at two dates: March 30 and May 11 of the new variety 'Planasa 0955' when compared to its closest varieties 'Sabrina' and 'Florida Radiance'.

| Variety | 30 March WEIGHT (g/fruit) | 11 May WEIGHT (g/fruit) |
|---|---|---|
| 'Planasa 0955' | 26 | 25 |
| 'SABRINA' | 27 | 25 |
| 'Honda Radiance' | 26 | 25 |

WEIGHT is shown as the average weight per fruit (g/fruit) in First Quality Fruits.

Table 5

Table 5 shows a comparison of the fruit analysis between the new variety 'Planasa 0955' and its closest varieties 'Sabrina' and 'Florida Radiance'.

| FRUIT ANALYSIS | | | |
|---|---|---|---|
| | 'Planasa 0955' (09.24.197) | 'Sabrina' | 'Florida Radiance' |
| Firmness (Kg) | 0.50 | 0.60 | 0.70 |
| Humidity & Volatile Matter (%) | 93.90 | 93.50 | 91.70 |
| Dry Matter (%) | 6.01 | 6.50 | 8.30 |
| pH (to 20°) | 3.50 | 3.50 | 3.50 |
| Acidity as Anhydride Citric (%) | 0.65 | 0.52 | 0.71 |
| Soluble Solids (°Brix) | 5.70 | 6.40 | 7.60 |
| Maturity Index | 8.80 | 12.30 | 10.70 |
| Content in Ascorbic Acid (ppm) | 111.30 | 402.90 | 256.40 |
| Dominant Tonality (nm) | 490 | 495 | 490 |
| Luminosity: Transmittance to 460 nm | 19.10 | 16.90 | 12.00 |
| Number of Units per kg | 43 | 28 | 42 |
| Median mass (g) | 24.2 | 35.8 | 24.0 |

The following definitions apply:

Firmness: It is the fruit's resistance to penetration measured in Kilograms (Kg). The measure given has been obtained by the penetrometer ROZE Mod. Arbelette, with a 50 $mm^2$ section head.

Dry Matter: It is the residual weight left from the trituration of the fruit after the drying process at a temperature of 103° C.±2° C. until reaching constant weight.

(%) Dry Matter=(Weight Dry Matter/Weight Fresh Matter)×100

Humidity & Volatile Matter: Represents the content in volatile matters and water of the fruits.

(%) Humidity & Volatile Matter=100−% Dry Matter

Maturity Index: Relation between Soluble solids and Acidity as Anhydride Citric.

Maturity Index=Soluble solids/Acidity as Anhydride Citric

DETAILED DESCRIPTION OF THE NEW VARIETY

The following additional information is provided to further describe the new variety:

Variety: 'Planasa 0955'.

Breeder Ref: 09.24.197.

Classification: *Fragaria* L.

Plant:

- *Growth habit*.—Upright.
- *Density of foliage*.—Dense.
- *Vigor*.—Strong.
- *Height*.—Medium, about 24 cm.
- *Width*.—Medium, about 21 cm.

Leaf:

- *Upper side color*.—Medium green; R.H.S. green group color (near 141 B to 143 A).
- *Underside color*.—R.H.S. yellow-green group color (near 146 B to 146 A).
- *Size*.—Medium.
- *Length*.—About 9 cm.
- *Width*.—About 15.5 cm.
- *Shape in cross section*.—Concave.
- *Leaf surface undulation or blistering*.—Absent or weak.
- *Number of leaflets*.—Three only.
- *Glossiness*.—Absent or weak.
- *Variegation*.—Absent.

Leaf stem characteristics:

- *Color*.—R.H.S. yellow-green group (near 144 C to 144 B).
- *Position of hairs*.—Upwards.
- *Length*.—Long, about 21.0 cm to 22.0 cm.

Terminal leaflet:

- *Length/width ratio*.—Much longer.
- *Length*.—Long, about 8.0 cm to 8.5 cm.
- *Width*.—Medium, about 5.0 cm to 5.5 cm.
- *Shape of base*.—Acute.
- *Margin*.—Serrate to crenate.
- *Shape in cross section*.—Concave.
- *Shape*.—Ovate with the apex rounded shaped and base acute shaped.
- *Apex*.—Rounded with the margin serrate to crenate.

Petiole:

- *Attitude of hairs*.—Upwards.
- *Color*.—R.H.S. yellow-green group (near 144 C to 144 B).
- *Length*.—Medium to long, about 21.0 cm to 22.0 cm.
- *Diameter: About* 2.0 mm to 3.0 mm.

Stipule:

- *Anthocyanin coloration*.—Weak, R.H.S. greyed-green group coloration (near 179 C to 179 B).
- *Length*.—Medium, about 3.0 cm to 3.5 cm.
- *Width*.—About 7.0 mm to 8.0 mm.

Stolons:
*Number*.—Medium, about 9.
*Thickness*.—Medium, about 3.5 mm to 4.0 mm.
*Pubescence density*.—Medium.
*Anthocyanin coloration*.—Absent or very weak, R.H.S. yellow-green group coloration (near 144 D to 144 C).
*Color*.—R.H.S. yellow-green group (near 144 D to 144 C).
*Length*.—Medium, about 33 cm to 36 cm.

Inflorescence:
*Number of flowers*.—Medium, about 6 to 8.
*Position relative to foliage*.—Level with.

Pedicel:
*Attitude/position of hairs*.—Upwards.
*Length*.—About 15.0 cm to 17.0 cm.
*Diameter*.—About 2.7 mm to 3.5 mm.
*Color*.—R.H.S. yellow-green group (near 144 D to 144 C).

Flower:
*Diameter/size*.—Medium.
*Size of calyx relative to corolla*.—Larger.
*Arrangement of petals*.—Overlapping.
*Diameter primary flowers*.—Long, about 3.1 cm to 3.6 cm.
*Diameter secondary flowers*.—Medium, about 2.7 cm to 3.1 cm.
*Number of petals*.—About 8 to 9.
*Fragrance*.—No significant fragrance.
*Time from bloom to mature fruit* (*in Huelva, Spain*).—About 30 days to 35 days.
*Stamens*.—Present and numerous with pollen present, fertile and abundant.
*Stamens length*.—Approximately 3.7 mm to 3.8 mm.
*Stamens color*.—R.H.S. white group (near 155 D to 155 C).
*Anthers*.—Generally average in size.
*Anthers color*.—R.H.S. yellow group (near 12 B to 12 A) and darkening with advanced maturity.
*Disposition of the anthers compared to the stamens*.—Above.
*Pollen*.—Fertile and abundant.
*Pollen color*.—R.H.S. yellow orange group (near 16 B to 16 A).
*Pistils*.—Abundant.
*Pistils size*.—Medium.
*Pistils color*.—R.H.S. yellow group (near 13 C to 13 B).

Petal:
*Length/width ratio*.—Equal.
*Length*.—Long, about 12 mm to 14 mm.
*Width*.—Long, about 11 mm to 13 mm.
*Shape*.—Rounded.
*Color of upper side*.—White; R.H.S. white group (near 155 C to 155 B).
*Apex*.—Rounded.
*Margin*.—Glabrous.
*Base*.—Rounded and get narrower.

Fruiting truss:
*Attitude*.—Semi-erect.

Fruit:
*Ratio of length/maximum width*.—Moderately longer.
*Color*.—Medium red; R.H.S. red group (near 44 B to 44 A).
*Peduncle length of inflorescence stem of primary fruit*.—About 18 cm to 20 cm.
*Peduncle length of inflorescence stem of secondary fruit*.—About 13 cm to 15 cm.
*Peduncle of inflorescence stem color*.—R.H.S. yellow-green group (near 144 D to 144 C).
*Peduncle diameter*.—About 2.2 mm to 2.6 mm.

Primary fruit:
*Length*.—Long, about 4.8 cm to 5.5 cm.
*Width*.—Medium, about 3.7 cm to 3.9 cm.

Secondary fruit:
*Length*.—Long, about 4.5 cm to 5.0 cm.
*Width*.—Medium, about 3.3 cm to 3.7 cm.
*Size*.—Medium to large.
*Shape*.—Conical.
*Difference in shapes between primary and secondary fruits*.—None to very slight.
*Width of band without achenes*.—Absent or very narrow.
*Color of achenes*.—R.H.S. orange to orange red group (near 33 C to 33 B).
*Evenness of surface*.—Even or very slightly uneven.
*Evenness of color*.—Even or very slightly uneven.
*Glossiness*.—Medium.
*Insertion/position of achenes*.—Below surface.
*Insertion of calyx*.—Level with fruit.
*Attitude of sepals*.—Upwards and outwards.
*Size/diameter of calyx in relation to diameter of fruit*.—Slightly smaller. The calyx presents 7 to 8 sepals with lanceolate shape and 4 to 5 sepals in addition smaller than above mencionated with pointed shape.
*Color upper side of sepals*.—Green group (near 141 B to 141 A).
*Color underside of sepals*.—Yellow-green group (near 144 B to 144 A).
*Length of sepals*.—Long, about 16 mm to 18 mm.
*Width of sepals*.—Long, about 6 mm to 8 mm.
*Sepal apex*.—Acuminate.
*Sepal margin*.—Smooth.
*Adherence of calyx*.—Strong.
*Firmness*.—Firm.
*Color of flesh* (*excluding core*).—Orange red; R.H.S. orange red (R.H.S. orange-red group near 33 B to 33 A), lightening toward center.
*Distribution of orange red color of flesh*.—Marginal.
*Fruit cavity/hollow center*.—Absent or small.
*Color of core*.—Light red; R.H.S. orange red group (near 32 C to 32 B).
*Sweetness*.—Medium. 5.70 ° Brix.
*Acidity*.—Medium. 0.65%.
*Time of flowering* (50% *of plants at first flower*).—Medium.
*Time of ripening* (50% *of plants with ripe fruits*).—Medium.
*Type of bearing*.—Not remontant.
*Chilling*.—Weak.

Disease resistance: No particular sensitivity to any disease or parasite has been observed for 'Planasa 0955'.

Storage qualities: 'Planasa 0955' fruit maintain their quality characteristics when keeping them in a frigo chamber at temperatures of about 2° C. during 48 hours. The fruit's color remains substantially the same.

Planting date: October 13 in Cartaya (Huelva), Spain, about 7° W, 37° N, 45 feet elevation (15 meters high).

10% Flowering (based on October 13 planting date): About November 23.

First mature fruits (based on October 13 planting date): About January 4.

Maturity (15-20 gms/plant)(based on October 13 planting date): About January 29.

Time of flowering data: Time of flowers (50% of plants at first flower)(based on October 13 planting date): About December 14.

Time of ripening (based on October 13 planting date): After planting as aforesaid, plants are grown in raised beds covered with plastic and with small holes in plastic walls, under tunnel. Water and fertilizer were applied through drip irrigation. Time of ripening (50% of plants with ripe fruit) is about January 18. First mature fruit is about January 4 and maturity (15-20 gms/plant) is about January 29.

I claim:

1. A new and distinct strawberry plant of the variety substantially as shown and described.

* * * * *